United States Patent [19]

Takeuchi

[11] Patent Number: 4,805,651
[45] Date of Patent: Feb. 21, 1989

[54] APPARATUS FOR DYEING SKELETONS OF ANIMAL FETUSES

[75] Inventor: Toshiyasu Takeuchi, Togura, Japan

[73] Assignees: Kabushiki Kaisha Tiyoda Seisakusho, Koushoku; Sakura Finetechnical Co., Ltd., Tokyo, both of Japan

[21] Appl. No.: 65,862

[22] Filed: Jun. 23, 1987

[30] Foreign Application Priority Data

Jun. 23, 1986 [JP] Japan ............... 61-94596[U]

[51] Int. Cl.⁴ ............................................. B08B 3/04
[52] U.S. Cl. ..................................... 134/98; 134/105; 134/183; 134/201; 118/429
[58] Field of Search ............... 118/429, 421, 697; 134/95, 104, 105, 182, 183, 198, 200, 201, 98

[56] References Cited

U.S. PATENT DOCUMENTS

| | | | |
|---|---|---|---|
| 1,335,853 | 4/1920 | Myrick | 134/182 X |
| 3,227,130 | 1/1966 | Weiskopf | 118/429 X |
| 3,294,101 | 12/1966 | Suzuki et al. | 134/96 X |
| 3,854,440 | 12/1974 | Astle | 118/429 X |
| 3,892,197 | 7/1975 | Kinney et al. | 118/429 X |
| 4,141,317 | 2/1979 | Louder et al. | 134/95 X |
| 4,483,270 | 11/1984 | Toya et al. | 118/429 X |
| 4,569,647 | 2/1986 | McCormick | 118/429 X |
| 4,604,964 | 8/1986 | Gordon et al. | 118/429 X |

Primary Examiner—Harvey C. Hornsby
Assistant Examiner—Frankie L. Stinson
Attorney, Agent, or Firm—Ladas & Parry

[57] ABSTRACT

An apparatus for dyeing the skeletons of animal fetuses with medical liquids includes a treating tank for accommodating a cage in which the fetuses are put, in which tank the medical liquids are circulated by a medical liquid pump. When fed into the treating tank, the circulating medical liquids are dispersed over the liquid surface. The skeleton-dyeing apparatus further includes a neutralization tank for neutralizing used-up medical liquids discharged from the treating tank.

11 Claims, 4 Drawing Sheets

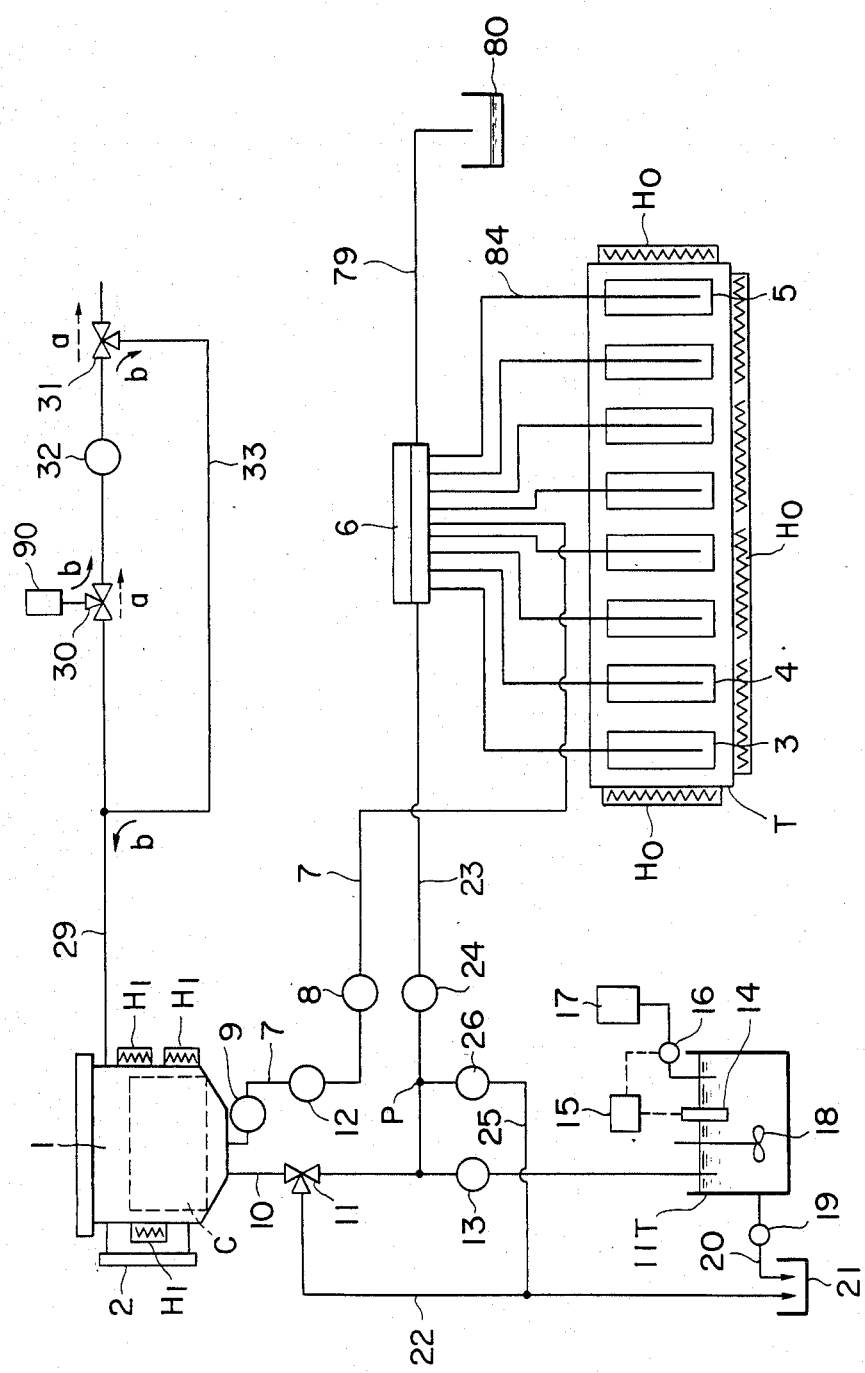
F I G. 1

4,805,651

APPARATUS FOR DYEING SKELETONS OF ANIMAL FETUSES

BACKGROUND OF THE INVENTION

This invention relates to an apparatus for dyeing the skeletons of the fetuses of an experimental animal such as a mouse for the purpose of teratogenic studies of animals.

For the teratogenic studies, the skeletons of the fetuses of a small animal such as a mouse are investigated in medical and pharmaceutical fields. To this end, the fleshy moieties of animal fetuses are dissolved out, and the bony moieties thereof are then dyed for easy observation or photographing.

When the skeletons collapse during treatment, it is impossible to grasp the overall shape thereof. Thus, the skeletons should be treated, while they are kept in shape.

With the foregoing in mind, the present inventors have invented an apparatus in which a treating liquid is circulated through a treating tank containing the fetuses of an animal to treat them without giving vibration thereto (Japanese Utility Model Kokai-Laid-Open-Publication Nos. 56-37588 and 57-152188).

In such a skeleton-dyeing apparatus, however, it is required to achieve uniform circulation of the treating liquid throughout the interior region of the treating tank. However, in the conventional apparatus simply designed to pour a treating liquid into a treating tank from the side thereof, its circulation became so uneven that there were variations in dyeing of the skeletons.

When a caustic potash solution of strong alkalinity is used to dissolve the fleshy moieties of fetuses with the conventional skeleton-dyeing apparatus, that caustic potash solution cannot be discharged as such to an effluent path (sewerage) for disposal, due to its strong alkalinity.

Hitherto, a waste liquid part of strong alkalinity has been stored in a separate vessel by an operator in the course of automatic operation of the apparatus, while another harmless waste liquid part has been discharged directly to an effluent path. For that reason, a piping line connecting the dyeing apparatus with the effluent path have had to be led to a separate vessel midway therebetween for receiving the waste liquid of strong alkalinity therein, thus causing a drop of efficiency.

SUMMARY OF THE INVENTION

A first object of the present invention is to provide an apparatus for dyeing the skeletons of animal fetuses, which assures uniform circulation of a treating liquid throughout the interior of a treating tank and thus enables uniform dyeing of animal skeletons.

A second object of the present invention is to provide an apparatus for dyeing the skeletons of animal fetuses, which allows a treating liquid of strong alkalinity to be automatically neutralized and discharged to an effluent path.

According to one aspect of the present invention, there is provided an apparatus for dyeing the skeletons of animal fetuses in which the animal fetuses are treated with various medical liquids to dissolve their fleshy moieties and dye their skeletons, and which comprises: (a) a treating tank adapted to accommodate a cage in which the fetuses of an animal are put and receive successively various medical liquids, and provided with a medical liquid-dispersing means for dispersing said medical liquids fed-in over the liquid surface; (b) a plurality of medical liquid tanks for storing various medical liquids; (c) a rotary valve for selectively communicating one of said medical liquid tanks to a pipe for feeding the associated medical liquid into said treating tank; and (d) a circulating piping system for circulating the medical liquid fed into said treating tank, which includes a circulating motor.

According to another aspect of the present invention, there is provided an apparatus for dyeing the skeletons of animal fetuses in which the animal fetuses are treated with various medical liquids to dissolve their fleshy moieties and dye their skeletons, and which comprises: (a) a treating tank adapted to accommodate a cage in which the fetuses of an animal are put and receive successively various medical liquids; (b) a plurality of medical liquid tanks for storing various medical liquids; (c) a rotary valve for selectively communicating one of said medical liquid tanks to a pipe for feeding the associated medical liquid into said treating tank; (d) a circulating piping system for circulating the medical liquid fed into said treating tank, which includes a circulating motor; (e) a neutralization tank for receiving a waste liquid from within said treating tank through a main discharge pipe; (f) a pH sensor provided to said neutralization tank for sending an electrical signal corresponding to a pH degree of said waste liquid; and (g) a pH controller for controlling supply of a counteractive from a counteractive vessel to said neutralization tank in response to said electrical signal from said pH sensor.

The nature, utility, and further features of this invention will be more clearly apparent from the following detailed description with respect to preferred embodiments of the invention when read in conjunction with the accompanying drawings briefly described below.

BRIEF DESCRIPTION OF THE DRAWINGS

In the accompanying drawings:

FIG. 1 is a schematical view showing the structure of the skeleton-dyeing apparatus according to this invention;

DETAILED DESCRIPTION OF THE INVENTION

Figure 2:
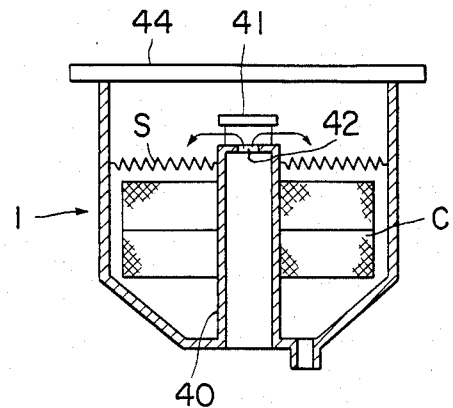
FIG. 2 is a view illustrating one interior structure of the treating tank.

Referring now to FIG. 1, various treating liquids are successively passed and circulated through a temperature-adjustable treating tank, generally shown at 1, including therein a cage C in which the fetuses of an animal are put. Pumps and valves are regulated by a known float switch 2 to adjust the upper and lower levels of the liquids in such a manner that overflowing of the liquids is prevented, and the fetuses are well-immersed in the liquids. Fed to the treating tank 1 are various treating liquids (medical liquids and water) from medical liquid-containing tanks 3, 4 and 5 placed in a box, generally shown at T, through a rotary valve 6. A heater $H_0$ is provided on and around the medical liquid box T to maintain the treating liquids at the predetermined temperatures. Connected to the rotary valve 6 is one end of an inlet pipe 7 for supplying the treating liquids into the treating tank 1, the other end of which pipe is in turn joined to the lower end of the treating tank 1. The inlet pipe 7 is further provided with electromagnetic valves 8, 9 and a circulating motor 12. On the other hand, a main discharge pipe 10 extends downward from the lower end of the treating tank 1, and terminates at its lower end in a neutralization tank 11T. The main discharge pipe 10 is fitted with a three-way valve 11 operated manually and an electromagnetic valve 13 in that order, as seen from above. The neutralization tank 11T is fitted with a pH sensor 14, which is adapted to send an electrical signal to actuate a pH controller 15 for opening or closing of an electromagnetic valve 16, whereby, when a strongly alkaline waste liquid such as caustic potash enters that tank 11T, a counteractive such as sulfuric acid is admitted thereinto from a counteractive vessel 17. The neutralization tank 11T includes therein a stirrer 18, and the liquid contained therein may be discharged through a pipe 20 to an effluent path 21 by opening of a valve 19.

From the three-way valve 11 of the main discharge pipe 10 positioned in the vicinity of the bottom of the treating tank 1, a first discharge branch pipe 22 extends to the aforesaid effluent path 21. The three-way valve 11 is provided to discharge the water supplied to the treating tank directly into the effluent path 21 without using pumps and other various valves/pipes, when it is intended to manually clean the treating tank, after automatic cleaning with the aforesaid pump 12. Upon opening of the three-way valve 11 relative to the discharge branch pipe 22, cleaning water is discharged directly to the effluent passage 21 through that pipe 22.

From an intermediate position between the three-way valve 11 and the electromagnetic valve 13 of the main discharge pipe 10, a return pipe 23 for returning the treating liquids contained the treating tank 1 to the associated treating-liquid tanks 3, 4 and 5 extends with the extreme end leading to the rotary valve 6. The return pipe 23 is provided at its intermediate position with an electromagnetic valve 24, and is connected to a second discharge branch pipe 25 at a point P just in front of the electromagnetic valve 24. The second branch pipe 15 then extends to the first discharge branch pipe 22, and is fitted with an electromagnetic valve 26.

Figure 5:
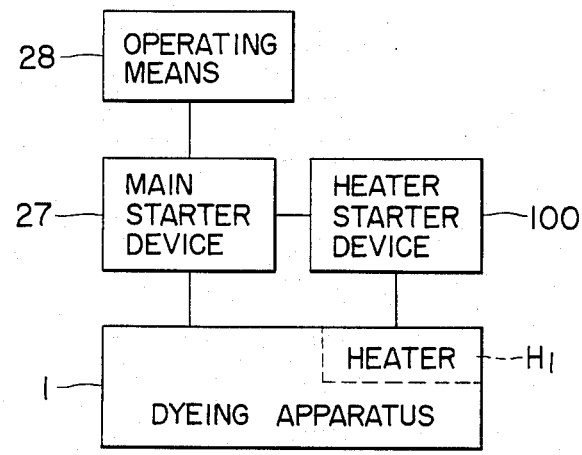
FIG. 5 is a block diagram illustrating the starting relationship between the skeleton-dyeing apparatus and the associated heaters.

On the side of the treating tank 1, there is mounted a heater $H_1$ which is connected to a heater starter device 100, as illustrated in FIG. 5. The heater starter device 100 is in turn connected with a main starter device 27 for the overall system, which is then connected to an operating means 28 of the overall system.

From an upper portion of the side of the treating tank 1, a vacuum-operated pipe 29 which is fitted with a pair of three-way valves 30 and 31 with a vacuum pump 32 interposed therebetween. A by-pass pipe 33 extends from one port of the three-way valve 31 toward the treating tank 1.

As shown in FIG. 2, the cage C is immersed into the treating tank 1, and is provided on the middle with a vertically extending injecting cylinder 40, which is connected at its lower end with the upper end of the aforesaid inlet pipe 7. Above the extreme end of that cylinder 40, there is placed a dispersion plate 41 which is designed to cover and injecting nozzle 42 formed on the upper end face of the injecting cylinder 40. The treating liquids injected out of the nozzle 42 strike against the back side of the dispersion plate, and are then spread over the surface S of the liquid contained in the treating tank 1. The thus achieved uniform circulation of the treating liquids through the tank assures uniform dyeing of the skeletons.

Figure 3:
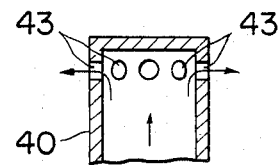
FIG. 3 is a view showing another embodiment of the injecting cylinder.
Figure 4:
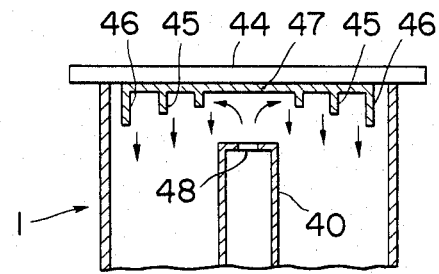
FIG. 4 is a view illustrating another interior structure of the treating tank.

It is to be understood that the injecting cylinder 40 may be designed to inject the treating liquid sideward from a number of small holes formed in the side of its extreme end portion, as illustrated in FIG. 3. It is also to be appreciated that a dispersion plate 47 having a ring-like arrangement of a plurality of projections 45 and 46 may be provided in the vicinity of a lid member 44 of the treating tank 1, as shown in FIG. 4. In this connection, it is noted that the projections 45 and 46 increase in length as they approach to the outer periphery of the dispersion plate 47. The treating liquids injected out of an nozzle 48 formed in the upper end portion of the injecting cylinder 40 strike against the respective projections 45 and 46, whence they fall down. This makes it possible to disperse the treating liquids uniformly within the treating tank 1.

Figure 7:
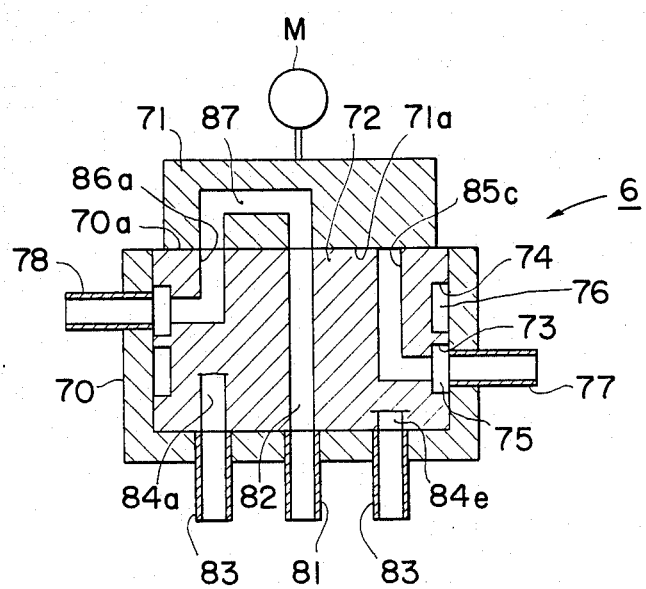
FIG. 7 is a longitudinally sectional view of the rotary valve.
Figure 8:
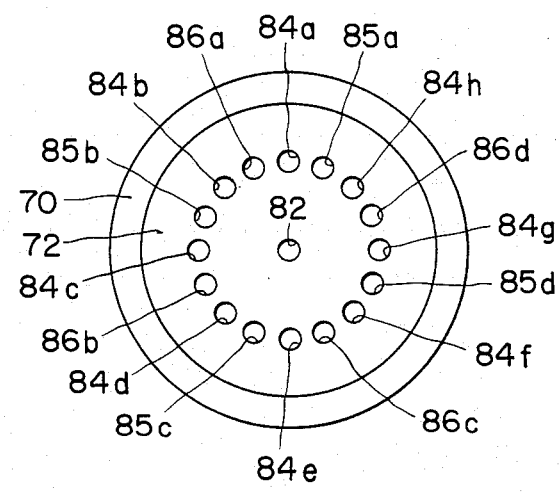
FIG. 8 is a plan view of the flow-path member of the rotary valve.

As illustrated in FIG. 7, the rotary valve 6 comprises a fixed base member 70 and a changeover plate 71 rotatingly driven by a motor M, while coming into liquid-tight and sliding contact with that base member.

The base member 70 includes a frame in the form of a short, bottomed cylindrical member, in which a flow-path member 72 is tightly fitted, said member 72 being in the form of a short column having a plurality of flow paths on the inside. On and around the overall outer periphery of the flow-path member 72, two grooves 73 and 74 are formed and spaced away from each other, and annular flow paths 75 and 76 are defined between them and the inner periphery of the frame 70. Provided through the outer wall of the frame 70 are a return port 77 to be connected with the return pipe 23 and an effluent port 78 to be connected with an effluent pipe 79 (FIG. 1), which has its extreme end open in an effluent tank 80.

A feed port 81 is provided through the middle of the bottom of the frame 70, and communicates with a first flow path 82 formed through the center of the flow path member 72. On the same circle with its center at the feed port 81, there are eight suction ports 83, 83 (only two of which are shown) at an equal angular interval. These suction ports 83 are connected to connecting pipes 84 extending from the respective treating liquid tanks 3, 4 and 5, and communicate with respective first eighth suction flow paths $84a$–$84h$. The ends of the flow paths $84a$–$84h$ are open in positions on the same circle on the end face $70a$ of the base member 70 with its center at the opening in the first flow path 82.

Four second flow paths $85a$–$85d$ (only one of which is shown in FIG. 7) formed in the flow-path member 72 are open at one end of each flow path 85 in a flow path 5 in which the return port 77 is open, and are open at the other end thereof on the same circular positions as those of the openings in the suction flow paths $84a$–$84h$ located on the end face $70a$ of the base member 70.

Four waste liquid flow paths $86a$–$86d$ (only one of which is shown in FIG. 7) are open at one end of each waste path 86 in the flow-path 76 in which a waste liquid port 78 is open, and are open at the other end thereof on the same circular positions as those of the openings in the suction flow paths 84a-84d and in the second flow paths 85a-85d, located on the end face 70a of the base member 70.

The changeover plate 71 having a plane 71a coming into liquid-tight, sliding contact with the aforesaid end face 70a is formed with a changeover flow path 87 which is open at one end in the central portion in alignment with the first flow path 82 and at the other end in a portion facing the circular positions where the respective suction, second and waste liquid flow paths are open. The changeover plate 71 is turned by the motor M, and the other end of the changeover flow path 87 is changed for communication with any one of the suction, second and waste liquid paths, while the one end remains communicated to the first flow path 82.

When the treatment for dyeing the skeletons is carried out with the single tank type skeleton-dyeing apparatus into the the rotary valve is incorporated in the manner as mentioned above, the changeover plate 71 is turned clockwisely or counterclockwisely by the motor M to select the flow paths through the changeover path 87.

Since the changeover plate 71 and flow-path member 72 of the rotary valve 6 are formed of a ceramic material, the valve 6 may not possibly be attacked by the medical liquids used, and shows increased wear resistance. This results in an increase in durability, prevents any liquid leakage, and dispenses with any sealing gasket. Due to the fact that the ceramic material may not possibly be damaged by dust and so on, it is very unlikely that the valve may be damaged by dust and so on.

As the treating medical liquids stored in the tanks 3, 4 and 5, use may be made of, for instance, 1% solutions of caustic potash, mixed liquids of caustic potash with alizarine red, Mall's liquids and glycerin solutions the concentrations of which are increased in the order of 30%, 50% and 80%. These liquids and cleaning water are stored in the respective tanks 3, 4 and 5 whence they are separately fed to the treating tank 1. The medical liquid tanks and treating tank 1 can be heated by the heater $H_1$. It is to be understood that motor valves adapted to be opened or closed by a motor may be used in place of the respective electromagnetic valves.

The operation of the apparatus according to the present invention will now be explained.

(a) Pre-heating of Treating Liquids

At the time of commencement of works such as extraction of the fetuses of an animal from the mother's uterus, the operating means 28, shown schematically in FIG. 5, is operated to set the dyeing apparatus in such a manner that it will be started at the predetermined time by the main starter device 27. In association with this operation, the heater starter device 100 is set in such a manner that it will be started at a time earlier than the aforesaid predetermined time by a time period corresponding to that required for temperature rises (e.g., 1.5 hours). Then, the heaters $H_0$ and $H_1$ will be started, e.g., 1.5 hours, before starting of the dyeing apparatus, whereby heating of the treating tank 1 and medical-liquid box T will be started.

After the lapse of a certain time, the fetuses of an animal to be treated, for instance, about 10 fetuses of a mouse, are put in the cage C, which is in turn placed in the treating tank 4, followed by lidding.

Figure 6:
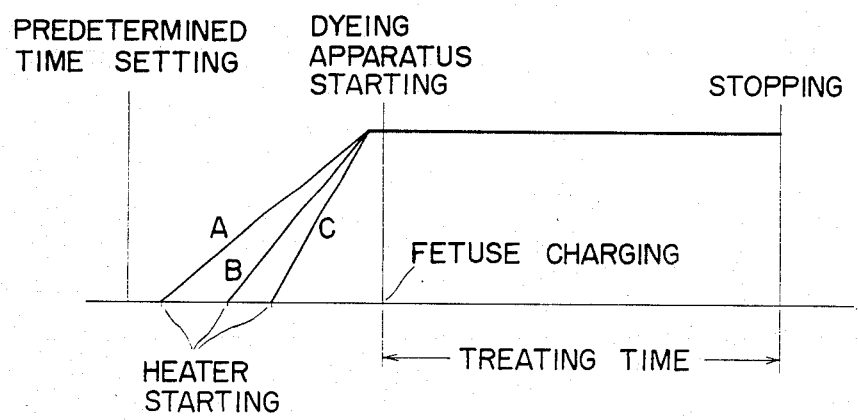
FIG. 6 is a graphical view showing the treatment achieved with the skeleton-dyeing apparatus.

This state is illustrated in FIG. 6. As illustrated schematically in this figure, the substantial treatment time can certainly be kept constant by putting the animal's fetuses into the treating tank 1 for the commencement of dyeing treatment, after the apparatus has indicated that the medical liquids reach the predetermined temperature (e.g., 30° C.).

(b) Feeding of Treating Liquids to Treating Tank 1

In order to supply the treating liquid (usually caustic potash) from the medical liquid tank 3 to the treating tank 1, the changeover plate 71 is operated to make communication between the suction flow path 84a and the first flow path 82, and the electromagnetic valves 8 and 9 of the inlet pipe 7 are opened, while other electromagnetic valves 13, 24 and 26 remain closed. In this state, the interior of the treating tank 1 is allowed to communicate with the vacuum pump 32 by the three-way valve 30 of the vacuum-operated pipe 29 in the direction shown by an arrow a in FIG. 1. Upon subsequent actuation of the pump 32, the air in the tank 1 is discharged in the direction indicated by the arrow a, resulting in a drop of the air pressure therein. This then allows the caustic potash solution contained in the tank 3 to be sucked into the treating tank 1 through the inlet pipe 7. As the liquid level ascends in the treating tank 1, the float of the float switch 2 ascends, correspondingly. Upon the liquid level reaching the upper limit position, the float switch 12 sends out an electrical signal, which turns the rotary valve 7 into the "closed" position, whereby the vacuum pump 32 is stopped to open the valves 8, 9 and 24.

(c) Circulation of Treating Liquids

Subsequent actuation of the pump 12 causes the caustic potash solution to circulate through the treating tank 1, pipes 10 and 23, valve 6 and pipe 7. Thus, that solution is passed through the cage C put in the treating tank 1 to dissolve the fleshy moieties of the fetuses. At this time, the treating liquid is injected out of the extreme end of the injecting cylinder, and falls down evenly onto the surface of the liquid in the treating tank 1. Provision of the liquid-dispersing device in the treating tank 1 thus assures uniform circulation of the treating liquid.

(d) Discharging of Strongly Alkaline Treating Liquid to Neutralization Tank

In the case that the treating liquid is a caustic potash solution of strong alkalinity, the pump 12 is stopped upon completion of dissolution of the fleshy moieties, thereby closing the valve 9 and opening the valve 13. Due to its own weight, the treating liquid in the treating tank flows down to the neutralization tank 11T through the three-way valve 11 and electromagnetic valve 13 and then the pipe 10. This waste liquid is controlled by the pH controller 15 for neutralization. Provision of such a neutralization path dispenses with such troublesome operation as required in the prior art, wherein the waste alkaline liquid is received in a separate vessel where it is neutralized. Since a centrifugal pump is usually used as the pump 12, the liquid can freely pass therethrough, when it is stopped. In the case that use is made of a pump which does not permit any liquid to pass therethrough, such as a vane pump, however, that pump must be reversed.

(e) Feeding and Discharging of Other Treating Liquids

Next, the changeover plate 71 is changed to make communication between the suction flow path 84b and the first flow path 82 of the rotary valve 6 leading to other medical liquid tank 4, followed by repetition of the operations as mentioned above, whereby the treating liquid in the tank 4 can be fed to the treating tank 1 for circulation. The same applies to the tank 5, etc.

In order to discharge the treating liquid for which any neutralization is not required, the valves 13 and 24 are closed, while the valve 26 is opened. Then, the three-way valves 30 and 31 are allowed to communicate with each other in the direction indicated by the arrow b in FIG. 1, following which the vacuum pump 32 is actuated. As a result, the atmospheric air admitted from the suction pipe 90 is fed into the treating tank 1 through the pipes 33 and 29, wherein the liquid surface is forced down. Thus, the treating liquid is discharged to the discharge path 21 through the pipes 10 and 23, point P and pipes 25 and 22.

It is to be understood that the treating liquid may be discharged into the effluent tank 80 through the rotary valve 6. At this time, the valves 13, 24 and 26 are closed, while the valves 8 and 9 are opened, and the changeover plate 71 is changed to establish communication between the first flow path 82 of the rotary valve 6 and the waste liquid flow path 86a.

After removal, from within the treating tank 1, of the skeletons which have been treated in this manner, the cleaning water stored in the associated tank is passed through to clean the treating tank as well as various valves and pumps. After use, the cleaning water is discharged through the first discharge branch pipe 22 via the three-way valve 11. The above members, that is, the valves, the motor, etc. except the three-way valve 11 can be operated by a computer.

It is to be appreciated that the vacuum-operated pipe 29 is not always needed. Supplying of the medical liquids into the treating tank 1 from the associated tanks amy be achieved by the circulating pump 12. However, application of vacuum in the treating tank 1 is preferable, since impregnation of the treating liquids into the fetuses is promoted by extraction of air from within the same.

I claim:

1. An apparatus for dyeing a skeleton of a fleshy, skeletal animal fetus by treating said animal fetus with various medical liquids to dissolve its fleshy moieties and dye its skeleton, said apparatus comprising:
   (a) a treating tank for receiving a cage in which a fetus of a fleshy, skeletal animal has been put and, successively, various medical liquids so as to have a liquid surface in the treating tank, said treating tank being provided with a medical liquid-dispersing means for dispersing said medical liquids when circulated thereto over said liquid surface;
   (b) a plurality of medical liquid tanks for respectively storing said medical liquids;
   (c) a circulating piping system for circulating said medical liquids, when communicated thereto, to said medical liquid-dispersing means, said system including a circulating motor;
   (d) a rotary valve for selectively communicating one of said medical liquid tanks at a time with said system for feeding said medical liquid thereof into said treating tank; and
   (e) a neutralization tank and a main discharge pipe means selectively connecting said neutralization tank to said treating tank for receiving into the former a waste liquid from the latter, said waste liquid comprising one of said medical liquids after receipt in said treating tank, said neutralization tank including a pH sensor for sending an electrical signal corresponding to a pH degree of said waste liquid and a pH controller for controlling supply of a counter active to said neutralization tank in said response to said signal.

2. An apparatus as defined in claim 1, wherein said main discharge pipe is provided through a three-way valve with a discharge branch pipe for guiding said waste liquid directly to a discharge path.

3. An apparatus for dyeing a skeleton of a fleshy, skeletal animal fetus by treating said animal fetus with various medical liquids to dissolve its fleshy moieties and dye it skeleton, said apparatus comprising:
   (a) treating tank for receiving a cage in which a fetus of a fleshy, skeletal animal has been put and, successively, various medical liquids;
   (b) a plurality of medical liquid tanks for respectively storing said various medical liquids;
   (c) rotary valve means for selectively communicating one of said medical liquid tanks at a time with said treating tank for feeding said medical liquid thereof into said treating tank;
   (d) neutralization tank and main discharge pipe means for receiving a waste liquid from within said treating tank into a neutralization tank through a main discharge pipe, said waste liquid comprising said various medical liquids;
   (e) a pH sensor provided to said neutralization tank for sending an electrical signal corresponding to a pH degree of said waste liquid; and
   (f) a pH controller, for controlling supply of a counteractive to said neutralization tank in response to said electrical signal from said pH sensor.

4. An apparatus as defined in claim 3, wherein said neutralization tank is provided with a stirrer.

5. An apparatus as defined in claim 3, further comprising a circulating circuit for circulating the medical liquid fed into said treating tank, which includes a circulating motor.

6. An apparatus for dyeing skeletons of animal fetuses in which the animal fetuses are treated with various medical liquids to dissolve their fleshy moieties and dye their skeletons, said apparatus comprising:
   (a) a treating tank accommodating therein a cage in which the animal fetuses are put, and adapted to receive successively various medical liquids so as to have a liquid surface in the treating tank,
   (b) a plurality of medical liquid tanks for storing therein the various medical liquids;
   (c) a circulating piping system connecting said medical liquid tanks and said treating tank;
   (d) a changeover valve provided in said piping system for selectively communicating one of said medical liquid tanks with said treating tank for feeding the medical liquid in said one medical liquid tank into aid treating tank;
   (e) means for maintaining said liquid surface in said treating tank at such a level that the cage and therefore the animal fetuses therein are immersed in the medical liquid fed into the treating tank; and
   (f) medical liquid-dispersing means provided in the treating tank, said liquid dispersing means including an injecting cylinder extending upwardly from the bottom of the treating tank so as to receive thereinto the medical liquid to be fed into the treating tank and inject the same upwardly, and a dispersion plate fixedly disposed above said liquid surface and the injecting cylinder for receiving from below the injected medical liquid to disperse and drop the same over the liquid surface, thereby to stir the medical liquid in the treating tank uniformly for uniform dyeing of the skeletons.

7. An apparatus as defined in claim 6, wherein said injecting cylinder is formed with a plurality of injecting holes through the periphery of its upper portion.

8. An apparatus as defined in claim 6, wherein said dispersion plate is formed on the lower surface thereof with a ring-like arrangement of a plurality of projections.

9. An apparatus as defined in claim 6, wherein said medical liquid tanks are accommodated in a medical liquid box and said treating tank and medical liquid box are provided with heaters which are actuated to increase the temperature of said medical liquid to a predetermined temperature before the animal fetuses are put in said treating tank.

10. An apparatus as defined in claim 6, wherein said treating tank is connected to a vacuum-operated pipe which is provided with a vacuum pump designed to be actuated to apply vacuum into said treating tank, when the medical liquids are fed from said medical liquid tanks into said treating tank.

11. An apparatus for dyeing skeletons of animal fetuses in which the animal fetuses are treated with various medical liquids to dissolve their fleshy moieties and dye their skeletons, said apparatus comprising:

(a) a treating tank accommodating therein a cage in which the animal fetuses are put, and adapted to receive successively various medical liquids, so as to have a liquid surface in the treating tank, (b) a plurality of medical liquid tanks for storing therein the various medical liquids;

(c) a circulating piping system connecting said medical liquid tanks and said treating tank;

(d) a changeover valve provided in said piping system for selectively communicating one of said medical liquid tanks with said treating tank for feeding the medical liquid in said one medical liquid tank into said treating tank;

(e) means for maintaining said liquid surface in said treating tank at such a level that the cage and therefore the animal fetuses therein a immersed in the medical liquid fed into the treating tank; and (f) medical liquid-dispersing means provided in the treating tank, said liquid dispersing means including an injecting cylinder extending upwardly from the bottom of the treating tank so as to receive thereinto the medical liquid to be fed into the treating tank and inject the same upwardly to disperse the same, thereby to stir the medical liquid in the treating tank uniformly for uniform dyeing of the skeletons.

* * * * *